US012731690B2

(12) United States Patent
Sharma et al.

(10) Patent No.: US 12,731,690 B2
(45) Date of Patent: Sep. 8, 2026

(54) MULTI-MODALITY NEURAL NETWORK FOR ALZHEIMER'S DISEASE CLASSIFICATION

(71) Applicant: Siemens Medical Solutions USA, Inc., Malvern, PA (US)

(72) Inventors: Rishabh Sharma, Houston, TX (US); Ludovic Sibille, Knoxville, TN (US); Rachid Fahmi, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 285 days.

(21) Appl. No.: 18/558,600

(22) PCT Filed: Oct. 12, 2021

(86) PCT No.: PCT/US2021/071815

§ 371 (c)(1),
(2) Date: Nov. 2, 2023

(87) PCT Pub. No.: WO2023/063969

PCT Pub. Date: Apr. 20, 2023

(65) Prior Publication Data

US 2024/0233945 A1 Jul. 11, 2024

(51) Int. Cl.

| | |
|---|---|
| ***G06K 9/00*** | (2022.01) |
| ***G06V 10/44*** | (2022.01) |
| ***G06V 10/764*** | (2022.01) |
| ***G06V 10/82*** | (2022.01) |
| ***G16H 30/20*** | (2018.01) |
| ***G16H 50/20*** | (2018.01) |

(52) U.S. Cl.

CPC ............. *G16H 50/20* (2018.01); *G06V 10/44* (2022.01); *G06V 10/764* (2022.01); *G06V 10/82* (2022.01); *G16H 30/20* (2018.01)

(58) Field of Classification Search

CPC ........ G16H 50/20; G16H 30/20; G06V 10/44; G06V 10/764; G06V 10/82

See application file for complete search history.

(56) References Cited

U.S. PATENT DOCUMENTS

2020/0037942 A1 2/2020 Howard
2020/0178918 A1 * 6/2020 Park ....................... A61B 6/563

FOREIGN PATENT DOCUMENTS

CN 110838108 A * 2/2020 ............. G06T 7/337
CN 111247595 A * 6/2020 ............. G16H 50/70
KR 102100699 B1 * 4/2020 ............. G16H 50/50

OTHER PUBLICATIONS

Li, Bin, et al. "A multi-branch convolutional neural network for detecting double JPEG compression." arXiv preprint arXiv:1710.05477 (2017). pp. 1-16.

(Continued)

*Primary Examiner* — Xin Jia

(57) ABSTRACT

A neural network (16) operating on volume data and using convolutional layers (24) may better classify conversion or Alzheimer's disease. The neural network (16) may be trained to operate on incomplete data. The neural network (16) may have a branching architecture (30-34) for more accurate classification given a variety of types of available data (20, 21) for a given patient.

9 Claims, 2 Drawing Sheets

(56) References Cited

OTHER PUBLICATIONS

Marinescu, Razvan V., et al. "The alzheimer's disease prediction of longitudinal evolution (TADPOLE) challenge: Results after 1 year follow-up." arXiv preprint arXiv:2002.03419 (2020). pp. 1-50.
Shen, Dinggang, Guorong Wu, and Heung-Il Suk. "Deep learning in medical image analysis." Annual review of biomedical engineering 19 (2017): 221-248.
Goenka, Nitika et al: "Deep learning for Alzheimer prediction using brain biomarkers"; Artificial Intelligence Review, Springer Netherlands, NL; vol. 54, No. 7, May 17, 2021 (May 17, 2021), pp. 4827-4871.
Fahmi R. et al: "The impact of multi-center PET data harmoniza-:tion on the classification performance of deep learning networks in neurological imaging"; Annual Congress of the European Association of Nuclear Medicine; vol. 46, Nov. 9, 2019 (Nov. 9, 2019).
Manhua, Lui et al: "Multi-Modality Cascaded Convolutional Neural Networks for Alzheimer's Disease Diagnosis", Neuroinformatics, Humana Press Inc, Boston; vol. 16, No. 3, Mar. 23, 2018 (Mar. 23, 2018), pp. 295-308.
Huang, Yechong et al: "Diagnosis of Alzheimer's Disease via Multi-Modality 3D Convolutional Neural Network"; Frontiers in Neuroscience; vol. 13, May 31, 2019 (May 31, 2019).
Arjun, Punjabi et al: "Neuroimaging Modality Fusion in Alzheimer's Classification Using Convolutional Neural Networks"; arxiv. org, Cornell University Library, 201 Olin Library Cornell University Ithaca, NY 14853, 1811.051; Nov. 13, 2018 (Nov. 13, 2018).
Altaf, Tooba et al: "Multi-class Alzheimer's disease classification using image and clinical features"; Biomedical Signal Processing and Control, Elsevier, Amsterdam, NL, vol. 43, Mar. 2, 2018 (Mar. 2, 2018), pp. 64-74.
Weiming, Lin et al: "Multiclass diagnosis of stages of Alzheimer's disease using linear discriminant analysis scoring for multimodal data", Computers in Biology and Medicine; vol. 134, Jul. 1, 2021 (Jul. 1, 2021).
International Search Report for Corresponding PCT Application No. PCT/US2021/071815, mailed Jul. 1, 2022.
Feng, L. et al., "A Robust Deep Model for Improved Classification of AD/MCI Patient", IEEE J Biomed Health Inform, 19(5), p. 1610-1616, doi:10.1109/JBHI.2015.2429556, Sep. 2015 (Sep. 2015).

* cited by examiner

MULTI-MODALITY NEURAL NETWORK FOR ALZHEIMER'S DISEASE CLASSIFICATION

BACKGROUND

The present embodiments relate to machine-learned model-based diagnosis of Alzheimer's disease. Early diagnosis of Alzheimer's disease gives physicians the opportunity to slow the progression of the disease by working on care planning with patients or by selecting the appropriate patients for clinical trials. However, early diagnosis prior to a patient converting from mild cognitive impairment to Alzheimer's disease is difficult and unreliable. There is no single feature of a potential Alzheimer's patient that will indicate their conversion.

Early diagnosis of a patient who will convert to Alzheimer's has been approached through many methods. These methods include regression/proportional hazards models, random forests, neural networks, disease progression models, other machine learning models, benchmarks, etc. Some of these results and methods are summarized in "The Alzheimer's Disease Prediction of Longitudinal Evolution (TADPOLE) Challenge: Results after 1 Year Follow-up." According to this challenge, the best overall predictor used statistical regression based on a series of features including cognitive tests, clinical diagnosis, magnetic resonance imaging (MRI) measurements, fluorodeoxyglucose (FDG) positron emission tomography (PET) measurements, Apolipoprotein (APOE) status, and cerebral spinal fluid (CSF) measurements. Neural networks in combination with multiple modalities are proposed in other predictors. Better classification for the prediction is desired. An additional limiting factor is the limited number and/or variety of scans available for a given patient, resulting in some predictors not operating for a given patient due to the lack of information.

SUMMARY

By way of introduction, the preferred embodiments described below include methods, systems, instructions, and non-transitory computer readable media for a neural network operating on volume data and using convolutional layers to better classify conversion or Alzheimer's disease. The neural network may be trained to operate on incomplete data. The neural network may have a branching architecture for more accurate classification given a variety of types of available data for a given patient.

In a first aspect, a method is provided for classifying for Alzheimer's disease with a neural network. At least a first type of image data representing at least a first volume of a patient is acquired and input into the neural network. The neural network has first and second input branches each including multiple layers. The first input branch is for the first type of image data, and the second input branch is for a second type of image data. A classification of the patient with respect to Alzheimer's disease is output from the neural network in response to the inputting. The neural network has an output portion having been trained to output the classification in response to the inputting of the first type of image data, the second type of image data, and both the first and the second type of image data. The classification is displayed on a display screen.

In one embodiment, both the first type of image data and the second type of image data are acquired. The first type of image data is input into the first input branch, and the second type of image data is input into the second input branch. The classification is output in response to the inputting of both the first and second types of image data. In a further embodiment, the first type of image data is a first type of positron emission tomography data, and the second type of image data is a second type of positron emission tomography data or magnetic resonance data.

In another embodiment, the first type of image data is volume data representing a three-dimensional region of the patient. The volume data is input to the first input branch. Two-dimensional image data may be used in other embodiments.

Various architecture modifications may be used. For example, the multiple layers of each of the first and second input branches include convolutional neural network layers.

In an embodiment, the classification is output as a prediction for conversion of the patient from mild cognitive impairment to Alzheimer's disease. The classification in other embodiments may benefit from input of cognitive test information for the patient to the neural network. For example, the cognitive test information is input to a pooling layer of the output portion where the output portion has a dense layer after the pooling layer. The cognitive test information may be input to other parts or types of layers. The classification is output in response to the inputting of the first type of image data and the inputting of the cognitive test information.

In another embodiment, the output portion has at least first, second, and third output branches for outputting the classification. The first output branch outputs the classification in response to first feature values output by the first input branch in response to the inputting of the first type of image data, the second output branch outputs the classification in response to second feature values output by the second input branch in response to the inputting of the second type of image data, and the third branch has a concatenation of the first and second feature values output by the first and second input branches. The third output branch outputs the classification. In one example layer arrangement for the different output branches, each of the output branches includes convolution, global pooling, and softmax layers.

In a second aspect, a system is provided for classifying for Alzheimer's disease with a neural network. A memory is configured to store the neural network as machine trained. An image processor is configured to classify for Alzheimer's disease by input of any one or more different modalities of data representing an interior region of the patient to the neural network. The neural network has different output branches for different combinations of the one or more different modalities. A display is configured to display the classification generated by the image processor.

In one embodiment, the neural network includes separate input branches for each of multiple ones of the one or more different modalities. A first one of the output branches is for feature values for a first one of the different modalities, a second one of the output branches is for feature values for a second one of the different modalities, and a third one of the output branches is for a combination of the feature values for the first and second ones of the different modalities.

In another embodiment, the data is volume data. The different modalities are (1) different types of positron emission tomography data or (2) positron tomography data and magnetic resonance data.

In yet another embodiment, each of the different output branches has multiple convolutional layers.

In a third aspect, a system is provided for classifying for Alzheimer's disease with a neural network. A memory is configured to store the neural network as machine trained. An image processor is configured to classify for Alzheimer's disease by input of any one or more different modalities of volume data representing three-dimensional, interior regions of the patient to the neural network. The neural network is a convolutional neural network. A display is configured to display the classification generated by the image processor.

In one embodiment, the different modalities are (1) different types of positron emission tomography data or (2) positron tomography data and magnetic resonance data.

In other embodiments, the neural network has different output branches for different combinations of the one or more different modalities. Each of the output branches having multiple convolutional layers. In a further modification, the neural network includes separate input branches for each of multiple ones of the one or more different modalities. A first one of the output branches is for feature values for a first one of the different modalities, a second one of the output branches is for feature values for a second one of the different modalities, and a third one of the output branches is for a combination of the feature values for the first and second ones of the different modalities.

In an embodiment, the neural network includes separate input branches for each of multiple ones of the one or more different modalities.

In yet another embodiment, the neural network includes a pooling layer having an input for cognitive function information and features from convolution layers of the convolutional neural network.

The present invention is defined by the following claims, and nothing in this section should be taken as a limitation on those claims. Features or aspects for one type of claim (e.g., method or system) may be used in another type of claim. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A multi-modality neural network is used for the classification (e.g., prediction) of Alzheimer's Disease. A convolution neural network and volumetric data (i.e., imaging data representing a three-dimensional region of the patient) are used to classify. For dealing with missing data, the architecture of the neural network may include input branches and/or output branches.

Figure 1:
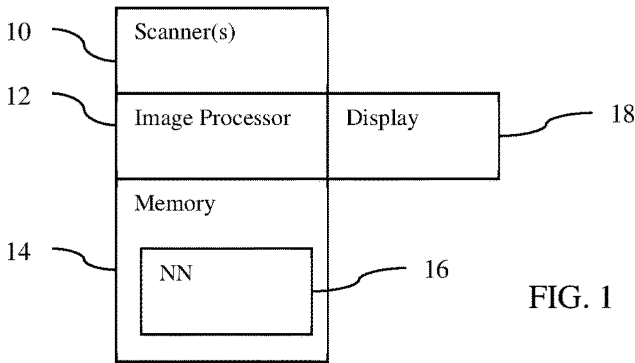
FIG. 1 is a block diagram of one embodiment of a system for classifying for Alzheimer's disease with a neural network.

FIG. 1 shows a block diagram of one embodiment of a system for classifying for Alzheimer's disease with a neural network. The system implements the method of FIG. 4 using the neural network 16 of FIG. 2, the neural network 16 of FIG. 3, or a different neural network 16. The neural network is a machine-learned model based on machine training to classify for Alzheimer's disease. The architecture of the neural network 16 is established to classify for Alzheimer's disease, such as using a convolutional neural network operating with input volume data (e.g., FIG. 2), a branching neural network (e.g., FIG. 3), or a combination thereof.

The system includes one or more scanners 10, an image processor 12, a memory 14, a display 18, and a machine-learned neural network 16. Additional, different, or fewer components may be provided. For example, a computer network or network connection is provided, such as for networking with a medical imaging network or data archival system or networking between the scanner 10 and the image processor 12. In another example, a user input is provided. As another example, the scanner 10 is not provided, where patient imaging data is stored in the memory 14 or accessed over a computer network. In yet another example, a server, workstation, or computer is provided for implementing the image processor 12 and/or neural network 16 remotely from the scanner 10.

The image processor 12, memory 14, and/or display 18 are part of the scanner 10. Alternatively, the image processor 12, memory 14, and/or display 18 are part of an archival and/or image processing system, such as associated with a medical records database workstation or server, separate from the scanner 10. In other embodiments, the image processor 12, memory 14, and/or display 18 are a personal computer, such as desktop or laptop, a workstation, a server, or combinations thereof.

The scanner 10 is a medical diagnostic imaging system. One or more scanners 10 are provided. For example, the scanner 10 is a positron emission tomography (PET) imager or a single photon computed tomography (SPECT) imager. A magnetic resonance (MR), computer tomography (CT), x-ray, ultrasound, or other type of medical scanner may be provided.

The scanner 10 is configured to scan the patient. The scan is performed to image an interior region of the patient. The scanner 10 is configured to output image data for the patient. Different scanners 10 or the same scanner may output different types or modes of image data.

A multi-modal source of information representing an interior region of the patient is provided. For example, a PET scanner acquires different types of image data, such as FDG PET and amyloid-PET (AV45) image data in two different modes. As another example, a PET scanner acquires one or more types of image data and a different type of scanner (e.g., MR) acquires one or more other types of image data. Any combination of different types of modes for one scanner and/or different modes or physics of scanning may be used. In one embodiment, the neural network 16 is configured by architecture to receive inputs of multi-modality medical images (e.g., a combination of two or more of FDG-PET, AV45, and MRI).

Any number of sets of image data representing a respective number of modes may be used. For example, one patient may have image data for one mode (e.g., FDG PET, AV45 PET, or MRI). Another patient may have image data for a different mode. Yet another patient may have image data for all or a combination of multiple modes.

Image data may include scan data, a reconstructed representation, and/or an image formatted for display on a display device. As scan data and/or a reconstructed representation, the image data may represent a volume or three-dimensional region of the patient. As scan data, a reconstructed representation, and/or data formatted for display, the image data may represent an area, plane, or two-dimensional region of the patient. Different sets of image data for different modes representing a same patient may represent the same, overlapping, or different volumes or other regions within the patient.

The memory 14 may be a graphics processing memory, a video random-access memory, a random-access memory, system memory, cache memory, hard drive, optical media, magnetic media, flash drive, buffer, database, combinations thereof, or other now known or later developed memory device (non-transitory) for storing data. The memory 14 is part of the scanner 10, part of a computer associated with the image processor 12, part of a database, part of another system, a picture archival memory, or a standalone device.

The memory 14 is configured to store data, such as in a computerized patient record. Any of the data discussed herein may be stored, such as the image data (e.g., image data representing a volume region or regions of the patient from multiple modalities) and/or patient-specific information (e.g., cognitive testing information). The memory 14 may store data during processing, such as storing values for features, values for learned parameters, neural network architecture, and information discussed herein or links thereto.

Figure 4:
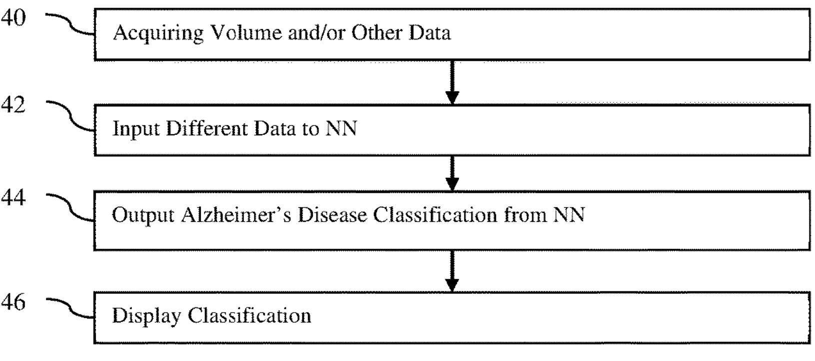
FIG. 4 is a flow chart diagram of one embodiment of a method for classifying for Alzheimer's disease with a neural network.

The memory 14 or another memory is alternatively or additionally a non-transitory computer readable storage medium storing data representing instructions executable by the programmed image processor 12 or a processor implementing the neural network 16 or acts of FIG. 4. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The memory 14 alternatively or additionally stores the neural network 16. The neural network 16 is stored as an architecture (e.g., layer structure, number of nodes, and links between layers and/or nodes) with fixed or previously learned values for learnable parameters, such as values for convolution kernels, weights, or combination functions.

The neural network 16 is a machine-trained model for classification. Machine learning uses training data of many hundreds or thousands of samples of inputs with labeled ground truth output or outputs for each sample. The training data is used as knowledge of past cases to train the classifier to generate the output for unseen cases. The training associates the features of the input vector with classification through learning values of learnable parameters in an optimization.

Any machine learning or training may be used. Any semi-supervised, supervised, or unsupervised learning may be used. Hierarchal or other approaches may be used. In one embodiment, the classification is by a machine-learned classifier learned with deep learning. As part of learning features of the neural network that distinguish between different classifiers, the classifier is also machine trained to output the class based on the learned features.

The machine learning trains the neural network to output a class for Alzheimer's disease. Any number of classes may be provided, such as normal, mild cognitive impairment, and Alzheimer's disease. The class may be predictive, such as the class being binary between conversion from mild cognitive impairment to Alzheimer's disease or not conversion likely to occur at a future time.

Any deep learning approach or architecture may be used. For example, a convolutional neural network is used. The network may include convolutional, sub-sampling (e.g., max pooling), fully connected or dense layers, softmax, and/or other types of layers. By using convolution, the number of possible features to be tested is limited. The fully connected layers operate to fully connect the features as limited by the convolution layer after maximum, average, or other pooling. Other features may be added to the fully connected or pooling layers, such as non-imaging or clinical information. Any combination of layers may be provided. Hierarchical structures are employed, either for learning features or representation or for classification or regression.

Figure 2:
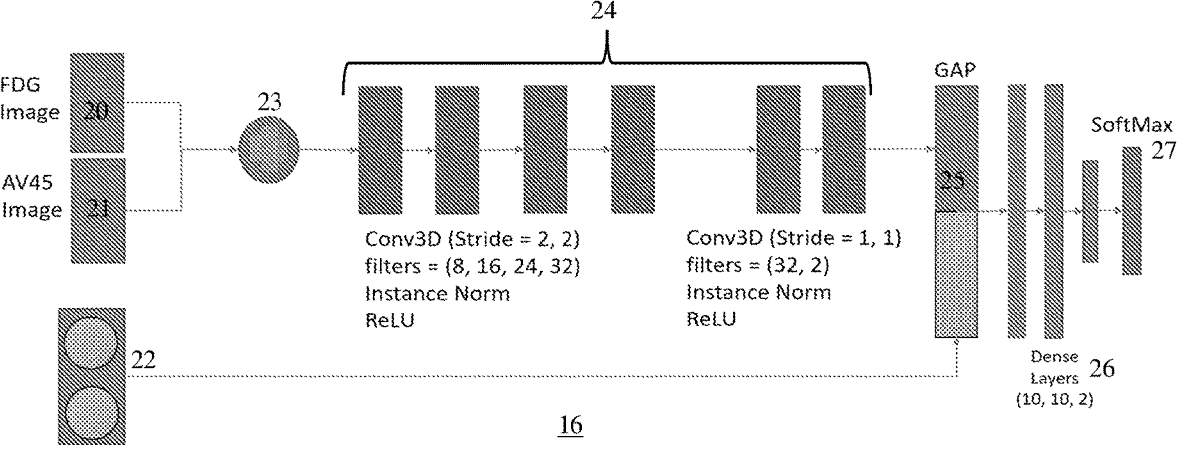
FIG. 2 illustrates one embodiment of a neural network architecture with convolution for Alzheimer's disease classification from volume data.

FIG. 2 shows one embodiment of a neural network. The neural network is a convolutional neural network, including one or more convolution layers 24. The convolution layers 24 filter or convolve a filter kernel of machine trained weights with input data (e.g., input image data or input feature values from a proceeding layer). In the example of FIG. 2, the FDG image data 20 and the AV45 image data 21 are volume data so the features and corresponding convolutions of the convolution layers 24 are three-dimensional convolutions, operating on volume data. For example, volumetric images of size 96×160×160 or other size from multiple modes (e.g., FDG PET and AV45 PET in this example) are concatenated 23 and input to the convolution layers 24. In the example of FIG. 2, the neural network has six convolution layers 24 followed by global average pooling layer 25 and three fully connected layers or dense layers 26 for a total of nine layers. A softmax layer 27 provides the output classification. Other types of layers and/or other numbers of layers in total or for any given type may be used. Stride=2, 2, the number of outputs by layer (e.g., 8, 16, 24, 32 for the first four convolution layers 24 and 32, 2 for the last two convolution layers 24), number of dense layers 26, type of pooling layer 25 (e.g., global average), and outputs of the dense layers 26 (e.g., 10, 10, 2) are provided as examples, but other numbers, outputs, strides, and/or types may be used.

The use of volume image data for input and/or convolution layers 24 may provide accurate classification for Alzheimer's disease. In other embodiments, convolution layers 24 are not used (e.g., neural network not being a convolutional neural network) and/or two-dimensional image data is used.

In the example of FIG. 2, the neural network provides input of cognitive function information 22 to the pooling layer 25. The pooling layer 25 receives values for features from the last convolution layer 24 and the cognitive function information. The input may be to a different layer, such as the fully connected or dense layers 26. Different clinical or cognitive function information 22 may be input to different layers.

Any cognitive function information may be input for a given patient. For example, the results from cognitive tests to identify mild cognitive impairment patients who will convert to Alzheimer's are input. The cognitive tests may be answers to a functional activity questionnaire (FAQ) and/or mini-mental state exam (MMSE) scores. Answers, scores, or other results for these and/or other cognitive tests may be used as input.

The neural network 16 is implemented by the image processor 12 or another processor with access to the neural network 16 stored in the memory 14 or other memory. The neural network 16 is defined as input channels (i.e., input vector), weights, relationships between weighted inputs or other layers, connections, filter kernels, and output channels and/or defined as architecture with values for learned and fixed parameters.

The machine-learned model, trained with or without deep learning, is trained to associate the categorical labels (output class for Alzheimer's disease) to the extracted values of one or more features from the inputs. The machine-learning uses training data with ground truth to learn to predict based on the input vector. The resulting machine-learned model defines how to extract values for features from the input and/or other features and output the class. In application, the neural network 16 generates the class in response to input of the available image data 20, 21 and/or the cognitive function information 22.

The image processor 12 is a general processor, central processing unit, control processor, graphics processor, artificial intelligence processor, digital signal processor, three-dimensional rendering processor, application specific integrated circuit, field programmable gate array, digital circuit, analog circuit, combinations thereof, or other now known or later developed device for applying a neural network. The image processor 12 is a single device or multiple devices operating in serial, parallel, or separately. The image processor 12 may be a main processor of a computer, such as a laptop or desktop computer, or may be a processor for handling some tasks in a larger system, such as in the scanner 10. The image processor 12 is configured by instructions, design, hardware, and/or software to perform the acts discussed herein.

The image processor 12 is configured classify for Alzheimer's disease by input of any one or more different modalities of volume data representing three-dimensional, interior regions of the patient to the neural network 16. Cognitive information 22 may also be input. The image processor 12, using the neural network 16, is configured to classify in response to the input. The output is a classification based on the input applied to the neural network 16.

The display 18 is a monitor, LCD, projector, plasma display, CRT, printer, or other now known or later developed devise for outputting visual information. The display 18 receives images of graphics, text, quantities, spatial distribution of anatomy, or other information from the image processor 12, memory 14, scanner 10, or neural network 16.

One or more images are displayed on the display 18. The images may or may not include anatomical or functional representation or imaging, such as an anatomical image from MR image data and a function image or images from PET image data. The image includes an indication, such as a text, a graphic, or colorization, of the classification of the patient for Alzheimer's disease.

Using the architecture of FIG. 2 and various training data collections, the neural network 16 was trained, and the results were tested for accuracy. The values of the learned parameters may be different when trained from different training data. Different architectures and/or different training data may result in different performance of the machine-learned neural network.

Using the architecture of FIG. 2, different combinations of input data: (i) FDG+AV45 PET images, (ii) FDG+AV45 PET images+FAQ Score, (iii) FDG+AV45 PET images+MMSE Score, and (iv) FDG+AV45 PET images+FAQ Score+MMSE Score are used for training and testing. The neural network 16 was trained on Alzheimer's (AD) vs Normal (NC) cases, and the inference results were calculated on the MCI (Stable (sMCI) or Progressed (pMCI)) cases for which all the input features (complete input vector) were available. AD and NC were inferred for a given MCI as pMCI will have similar imaging characteristics as AD while sMCI may never progress towards AD and will be closer to NC. It is possible to enrich the training data (NC+sMCI) vs (AD+pMCI) to fine-tune classification. Additional classes with sMCI and pMCI (both training and test data) may be added or used instead of AD and NC. Classification sensitivity, specificity, accuracy, and area-under-the-curve (AUC) for the considered marker combinations above were as follows: (i) 89.5, 64.8, 86.6, 84.2 (ii) 87.3, 68.5, 85.1, 83.5 (iii) 97.3, 46.3, 91.2, 86.9 (iv) 96.3, 50.0, 90.8, 87.0. A significant difference was seen where MMSE scores are included. High accuracy results for identifying the sMCI cases when MMSE scores were included in the models, but the pMCI cases were better identified when only image inputs were used.

Figure 3:
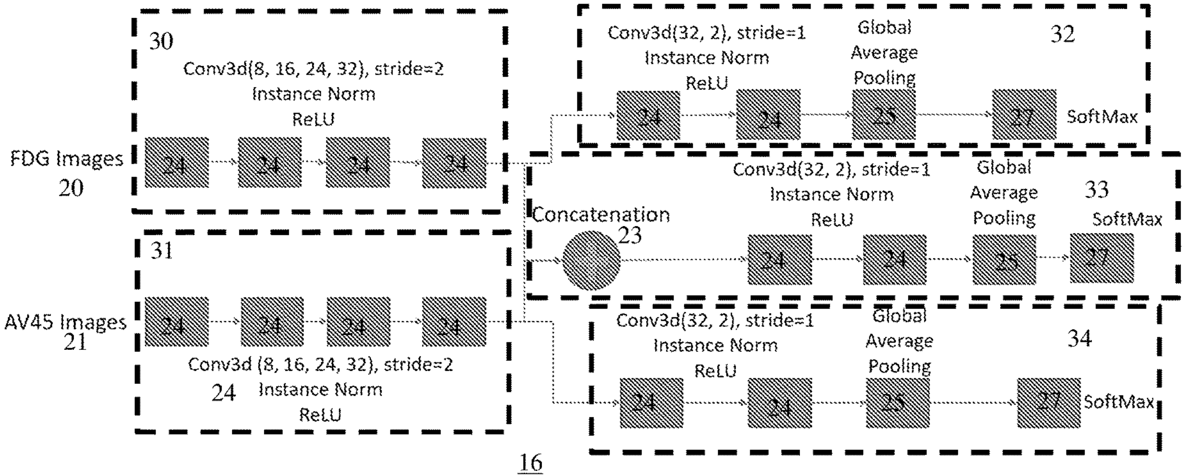
FIG. 3 illustrates an embodiment of a neural network architecture with input and output branches for Alzheimer's disease classification.

The system of FIG. 1 may be used with a different neural network 16. Different types of information (e.g., different types of image data) may be available for different patients. While the neural network of FIG. 2 may be trained to accept different available types of image data with or without cognitive function information 22 (e.g., use default values for missing data), the architecture may be altered to better handle variation in the types of information input. FIG. 3 shows an example. Using different input branches 30, 31, different output branches 32, 33, 34, or both different input branches 30, 31 and different output branches 32, 33, 34, the machine-trained neural network may better estimate the class despite variation in available data for input.

Additional, different, or fewer branches 30-34 may be used. Two or more input branches 30, 31 for a respective two or more different types (e.g., modes) of image data may be provided. Two or more (e.g., one more than the number of input branches 30, 31) output branches 32, 33, 34 may be used. In other embodiments, only one input branch (see FIG. 2 concatenation) or only one output branch 33 is used. The image data is volume data but may be 2D data.

In the example of FIG. 3, the input includes two different modes or types of image data. FDG image data 20 and AV45 image data 21 are input to separate, respective branches 30, 31. Instead of image data for two modes of PET (e.g., FDG and AV45), the image data may be for one or more modes of PET and one or more modes of MRI. Other types or modes of image data may be used.

The separate input branches 30, 31 are independent of each other where no data is shared between the branches 30, 31. The layers (e.g., convolution layers 24) and nodes of each branch 30, 31 are separate for calculating features for one of the different modalities. In the example of FIG. 3, each input branch 30, 31 is formed by four convolution layers for operating on volume data with output filters of 8, 16, 24, and 32 (e.g., 96×160×160 input image with output filter of 1×96×160×160×8 so having $1\times8\times3^3$ trainable parameters), stride=2, using instance norm, and ReLU activation. Other types of layers, numbers of layers, output sizes, strides, norms, and/or activations may be used. The same or different layer structure is used in each branch 30, 31. In alternative embodiments, values of features from one or both input branches 30, 31 are communicated to the other input branch 30, 31. The branches 30, 31 are still separate structures, but share some information.

Each input branch 30, 31 is for different possible image data that may be input. For a given patient, image data for one or more (e.g., less than all) of the branches 30, 31 may not be available and thus may not be input. If data is sparse (i.e., not all patients have the same number of scans and tests at a given time point), the neural network 16 can be trained using all available data in a way that utilizes multiple training branches 30-34 contributing to the overall network decision. Different branches 30-34 take different data as input depending on the availability. This branching in a trained neural network allows for classification even where the data for a given patient is sparse (i.e., missing one or more types of image data and/or cognitive function information). The two different image data input branches 30, 31 operate on two different types of image data, and the three different output branches 32, 33, 34 take feature values from different combinations of the input branches 30, 31 as input for classifying from either FGD images (output branch 32), AV45 images (output branch 34), or combined (concatenation 23) FDG and AV45 images (output branch 33) when both types of image data are available. Sparse data may be used to train as well. This way, no data will be thrown away and all samples, even sparse ones, may be used to train the neural network 16.

The separate output branches 32, 33, 34 are independent of each other where no data is shared between the branches 32, 33, 34. The layers (e.g., convolution layers 24, pooling layer 25, and softmax layer 27) and nodes of each branch 32, 33, 34 are separate for calculating features and classifying. In the example of FIG. 3, each output branch 32, 33, 34 is formed by two convolution layers for operating on volume data with convolutional filters (output) of 32 and 2, stride=1, using instance norm, and ReLU activation. Other types of layers (e.g., dense or fully connected layers between pooling layer 25 and softmax layer 27), numbers of layers, output sizes, strides, norms, and/or activations may be used. The output branches 32, 33, 34 each have a same layer structure but may have different layer structures. In alternative embodiments, values of features from one, multiple, or all output branches 32, 33, 34 are communicated to one or more other output branches 32, 33, 34. The output branches 32, 33, 34 are still separate structures (different layers and/or nodes make up the branch 32, 33, 34), but share some information.

Each output branch 32, 33, 34 is for a same classification. All three output branches 32, 33, 34 of FIG. 3 estimate the class from the same set of classes. Each output branch 32, 33, 34 operates on feature values for different combinations of input data. For example, the output branch 32 is for feature values output by the input branch 30 for FDG image data 20, the output branch 34 is for feature values output by the input branch 31 for AV45 image data 21, and the output branch 33 is for a combination or concatenation 23 of the feature values output by both input branches 30, 31 for both FDG image data 20 and AV45 image data 21. Where more than one output is provided, the estimated classes from the different outputs may all be used, combined to one class (e.g., priority or median), or only one used.

For a given patient, image data 20, 21 for one or more (e.g., less than all) of the branches 30, 31 may not be available and thus may not be input. For example, patient X has FDG image data 20 but not AV45 image data 21 available. The FDG image data 20 is input to the input branch 30, which outputs feature values to the output branches 32 and 33. Since features from input branch 31 are not available, the output branch 32 outputs the class from the softmax layer 27. For only AV45 image data 21 being available, the input branch 31 and output branch 34 are used. For both AV45 image data 21 and FDG image data 20 being available, both input branches 30, 31 and the combination output branch 33 are used to classify. Regardless of the type of data available, the architecture allows output of identity MCI patients who will convert to Alzheimer's disease or other classification.

Cognitive function information and/or clinical data may be used as an input. For example, the arrangement of FIG. 2 is used. The values for cognitive or clinical information are input to the pooling layers 25 of each of the output branches 32, 33, 34. One or more dense layers 26 are added between the pooling layer 25 and the softmax layer 27 in each of the output branches 32, 33, 34. When cognitive or clinical information is unavailable for a given patient, a default or zero padding may be used to allow classification.

Other neural network 16 arrangements may be used. For example, the neural network 16 of FIG. 2 is used as the architecture for the output branches 32, 33, 34 in FIG. 3. As another example, the convolution layers 24 of FIG. 2 are used as the input branches 30, 31 of FIG. 3.

The neural network 16, with the branching structure, has the advantage of handling missing data and making use of all available data. It also allows the incorporation of additional tests and scores. Multi-branching and multi-modality support allows the network to mimic the behavior of a physician to look at different information sources to make a final decision, which is considered more reliable compared to using a single modality.

The branching structure allows training using samples or training data with different sparsity. Multiple types of images and combinations are used to train the neural network 16. The loss is based on the class from the output branch 32, 33, 34 appropriate for the image data available for a given training sample (i.e., through a respective image output branch 32, 34 or the combination output branch 33). Joint loss may be used for classes output from more than one output branch 32, 33, 34 for a given training sample. This allows for training of the neural network 16 with training samples having limited data points. The branching helps in training and updating the weights (i.e., values of learnable parameters) for different branches 30-34 when the multiple data points are available. For example, if FDG image data and AV45 image data are both available, the input branch 30 that extracts features from FDG image data 20 also learns representation from AV45 image data during back the propagation step in optimization for training.

Using the architecture of FIG. 3, the neural network 16 was trained using Alzheimer's disease (AD) vs normal condition (NC) cases. The training set used all the available data points with either a single input volume (e.g., FDG-PET or AV45-PET) or a combination of both FDG-PET and AV45-PET volumes. The validation used only cases that had both FDG-PET and AV45-PET volumes to assess the performance of each branch on the test set. Classification Sensitivity, Specificity, Accuracy, and Area-under-the-curve (AUC) averaged over 10 folds were as follows: (i) FDG branch: 93.1, 88.9, 91.4, 95.4, (ii) AV45 Branch: 96.5, 74.9, 90.3, 94.1 (iii) Concatenated Feature Branch: 94.4, 86.5, 91.6, 96.1.

FIG. 4 is a flow chart of one embodiment of a method for classifying for Alzheimer's disease with a neural network. Using volume data, a convolutional neural network, and/or branching architecture, a patient's current or predicted class for Alzheimer's disease is determined with a neural network.

A medical scanner performs the acts. Alternatively, or additionally, a workstation, server, or other computer performs one or more of the acts. In one embodiment, the system of FIG. 1 performs the acts. For example, a PET scanner performs act 40. An image processor performs acts 42 and 44. A display screen performs act 46. Other devices may perform or be used in performance of any of the acts.

The acts are performed in the order shown (e.g., top-to-bottom or numerical) or other orders. Additional, different, or fewer acts may be provided. For example, the method is performed without act 46. As another example, acts for configuring a medical scanner are provided. In yet another example, acts for using or applying the output classification are provided.

In act 40, one or more sets of image data are acquired. The image data is a frame of data representing the patient. The data may be in any format. While the terms "image" and "imaging" are used, the image or imaging data may be in a format prior to actual display of the image. For example, the image data may be a plurality of scalar values representing different locations in a Cartesian or polar coordinate format (i.e., scan or voxel data) different than a display format. As another example, the image data may be a plurality red, green, blue (e.g., RGB) values output to a display for generating the image in the display format. The image data may be scan data, reconstructed data, a not yet displayed image, a currently displayed image, or a previously displayed image in the display or other format. The image or imaging is a dataset that may be used for anatomical or functional imaging.

The image data is obtained by loading from memory and/or transfer via a computer network. For example, previously acquired scan data is accessed from a memory or database. As another example, data for a reconstructed representation is transmitted over a network after acquisition from scanning a patient. In other embodiments, the image data is obtained by scanning the patient.

Any type of image data may be used. In one embodiment, the image data is PET, SPECT, CT, ultrasound, or MR data. For example, FDG-PET, AV45-PET, and/or MR data is acquired. More than one type of image data may be acquired. Data from different imaging modes is acquired, such as acquiring two types of PET image data or one or more types of PET image data and one or more types of MR image data.

One, more, or all of the types of image data represents respective volumes of the patient. Different types of image data from different scans may represent the same, overlapping, or different volumes. Three-dimensional representations of the patient is obtained. Alternatively, one or more types of image data represent a two-dimensional cross-section of the patient or a rendered view of the patient. Data representing an interior region of a patient is obtained.

In act 40, the image processor may acquire cognitive and/or clinical information for the patient in addition to the image data. Patient-specific information is acquired by mining, loading, input, or another source. For example, patient-specific information is loaded from a computerized medical record for the patient and/or solicitation of input from a user.

By obtaining patient-specific information, personalized information may be used. Various types of patient-specific information may be acquired. For example, patient attributes are acquired for the patient being scanned. The size, age, sex, cardiac output, other clinical measures, other characteristics of the patient's body, medical history, family medical history, and/or genetics are acquired as patient attributes. Cognitive information may be acquired, such as FAQ, MMSE, and/or other cognitive testing information. Non-image information is acquired.

In act 42, the acquired data is input to a neural network, such as the deep machine-learned neural network of FIG. 2 or 3. The neural network has any number of layers with or without separate input branches and/or output branches. In one embodiment, the neural network is a convolutional neural network. One or more layers are convolution layers.

The image data is input to the neural network. Where multiple types of image data are available, then the multiple types are input. Where only one type is available, then the one type is input. The input image data represents volume regions of the patient, but 2D image data may be used.

In one embodiment, the different types of image data are input to different input branches of the neural network. Each input branch has multiple layers. Different input branches may have different numbers and/or types of layers. One input branch is for one type of image data, and another input branch is for another type of image data. The different types of image data are input to the respective input branches.

Cognitive, clinical, or other types of information may also be input. For example, cognitive test (e.g., MMSE or FAQ) scores, answers, measurements, or results are input to the neural network. The input may be to any part of the neural network. In one embodiment, the input of non-image data is to one or more pooling layers. One or more dense or fully connected layers are provided after (e.g., immediately after) the pooling layer.

In act 44, the neural network outputs a classification of the patient with respect to Alzheimer's disease. Any classification may be used. In one embodiment, the classification is a prediction for conversion of the patient from mild cognitive impairment to Alzheimer's disease. The classes are no conversion and conversion. In other embodiments, the classes are current mild cognitive impairment or Alzheimer's disease.

The class is output in response to the input of act 42. The image processor calculates values for features through the layers, such as convolving input image data with machine-learned filter kernels. The features for sequential layers are sequentially determined until the softmax or other output layer outputs the class.

In one embodiment, the neural network includes an output portion trained to output the classification in response to the inputting of one type of image data, another type of image data, and both types of image data. Different branches are provided for outputting the classification based on what types of data were input to the neural network. For example, the output branching architecture of FIG. 3 is used with or without the input branching. Feature values for any branch associated with the available input data are calculated. One of the output branches corresponds to the available input data, so that output branch generates the classification. The classification may be responsive to any combination of types of image data. The classification may be responsive to input of cognitive test or clinical information.

In act 46, the classification is transmitted. The transmission is to a display, such as a monitor, workstation, printer, handheld, or computer. The classification is displayed on a display screen. Alternatively, or additionally, the transmission is to a memory, such as a database of patient records, or to a network, such as a computer network. Other outputs of the classification may be provided.

The transmission or display provides information for physician decision. The display may show one or more images of the patient as well as the machine-learned model estimated classification for that patient. The classification is provided as text, graph, color-coding, or other indication of class membership.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for classifying for Alzheimer's disease with a neural network, the method comprising:

acquiring at least a first type of image data representing at least a first volume of a patient;

inputting the first type of image data into the neural network, the neural network having first and second input branches each including multiple layers, the first input branch being for the first type of image data and the second input branch being for a second type of image data;

outputting a classification of the patient with respect to Alzheimer's disease from the neural network in response to the inputting, the neural network having an output portion having been trained to output the classification in response to the inputting of the first type of image data, the second type of image data, and both the first and the second type of image data, wherein outputting the classification comprises outputting from the output portion comprising at least first, second, and third output branches for outputting the classification, the first output branch for outputting the classification in response to first feature values output by the first input branch in response to the inputting of the first type of image data, the second output branch for outputting the classification in response to second feature values output by the second input branch in response to the inputting of the second type of image data, and the third output branch having a concatenation of the first and second feature values output by the first and second input branches, the third output branch outputting the classification; and displaying the classification on a display screen.

2. The method of claim 1 wherein acquiring comprises acquiring the first type of image data and the second type of image data, wherein inputting comprises inputting the first type of image data into the first input branch and inputting the second type of image data into the second input branch, and wherein outputting comprises outputting the classification in response to the inputting of both the first and second types of image data.

3. The method of claim 2 wherein acquiring comprises acquiring the first type of image data as a first type of positron emission tomography data and acquiring the second type of image data as a second type of positron emission tomography data or magnetic resonance data.

4. The method of claim 1 wherein acquiring comprises acquiring the first type of image data as volume data representing a three-dimensional region of the patient, and wherein inputting comprises inputting the volume data to the first input branch.

5. The method of claim 1 wherein inputting comprises inputting where the multiple layers of each of the first and second input branches comprise convolutional neural network layers.

6. The method of claim 1 wherein outputting comprises outputting the classification as a prediction for conversion of the patient from mild cognitive impairment to Alzheimer's disease.

7. The method of claim 1 further comprising inputting cognitive test information for the patient to the neural network, and wherein outputting comprises outputting the classification in response to the inputting of the first type of image data and the inputting of the cognitive test information.

8. The method of claim 7 wherein inputting the cognitive test information comprises inputting to a pooling layer of the output portion, the output portion having a dense layer after the pooling layer.

9. The method of claim 1 wherein the first, second, and third output branches comprise convolution, global pooling, and softmax layers.

* * * * *